(12) United States Patent
Duckett, III et al.

(10) Patent No.: US 10,051,166 B2
(45) Date of Patent: Aug. 14, 2018

(54) LIGHT DEVICE AND SYSTEM FOR PROVIDING LIGHT TO OPTICAL SCOPES

(71) Applicant: KARL STORZ Imaging, Inc., Goleta, CA (US)

(72) Inventors: George E. Duckett, III, Castaic, CA (US); Marc Amling, Santa Barbara, CA (US); Dashiell Birnkrant, Worcester, MA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 72 days.

(21) Appl. No.: 15/140,265

(22) Filed: Apr. 27, 2016

(65) Prior Publication Data

US 2017/0318205 A1 Nov. 2, 2017

(51) Int. Cl.
| | |
|---|---|
| *A61B 1/06* | (2006.01) |
| *H04N 5/225* | (2006.01) |
| *G02B 23/26* | (2006.01) |
| *G02B 23/24* | (2006.01) |
| *A61B 1/05* | (2006.01) |
| *A61B 1/045* | (2006.01) |
| *H02J 7/02* | (2016.01) |

(52) U.S. Cl.
CPC ........... *H04N 5/2256* (2013.01); *A61B 1/045* (2013.01); *A61B 1/05* (2013.01); *A61B 1/0669* (2013.01); *A61B 1/0684* (2013.01); *G02B 23/2453* (2013.01); *G02B 23/2469* (2013.01); *G02B 23/26* (2013.01); *H02J 7/025* (2013.01); *A61B 1/0638* (2013.01)

(58) Field of Classification Search
CPC ............ A61B 1/00016; A61B 1/00029; A61B 1/00121; A61B 1/042; A61B 1/128; A61B 1/0669; A61B 1/0684; A61B 1/0638; H04N 5/2256; H04N 2005/2255; G02B 23/2484
See application file for complete search history.

(56) References Cited

U.S. PATENT DOCUMENTS

| | | | | |
|---|---|---|---|---|
| 5,001,556 | A * | 3/1991 | Nakamura | A61B 1/00009 348/70 |
| 5,078,150 | A * | 1/1992 | Hara | A61B 1/00009 348/70 |
| 5,311,859 | A * | 5/1994 | Monroe | A61B 1/042 348/75 |
| 6,092,722 | A * | 7/2000 | Heinrichs | A61B 1/00016 235/375 |
| 6,141,037 | A * | 10/2000 | Upton | A61B 1/00016 128/908 |
| 6,398,724 | B1 * | 6/2002 | May | A61B 1/00188 600/112 |

(Continued)

*Primary Examiner* — John P Leubecker
(74) *Attorney, Agent, or Firm* — Michael Joseph Loi

(57) ABSTRACT

A system and method for providing light to an optical scope having a lightport. A light device connects a camera to an optical scope and supplies light to the scope while allowing for scope rotation. The light device has a proximal end attached to the distal end of the camera, a distal end adapted to be attached to and detached from the scope, and a light source. The light source may be powered by electrical power received from the camera. A light cable extends from the light device and has a distal end adapted to be attached to and detached from the light post on the scope to supply light to the scope. The distal end of the light device is rotatable with respect to the distal end of the camera such that the light cable is able to rotate about the optical axis of the camera.

14 Claims, 7 Drawing Sheets

(56) References Cited

U.S. PATENT DOCUMENTS

| | | | |
|---|---|---|---|
| 6,554,765 B1 * | 4/2003 | Yarush | A61B 1/00039 |
| | | | 348/73 |
| 6,692,431 B2 | 2/2004 | Kazakevich | |
| 6,921,920 B2 * | 7/2005 | Kazakevich | A61B 1/0607 |
| | | | 257/81 |
| 7,442,167 B2 | 10/2008 | Dunki-Jacobs et al. | |
| 7,668,450 B2 | 2/2010 | Todd et al. | |
| 8,029,439 B2 | 10/2011 | Todd et al. | |
| 8,246,230 B2 | 8/2012 | Todd et al. | |
| 8,301,229 B2 * | 10/2012 | Gono | A61B 1/00009 |
| | | | 356/300 |
| 8,363,097 B2 | 1/2013 | Kazakevich et al. | |
| 8,599,250 B2 | 12/2013 | Amling et al. | |
| 8,723,936 B2 | 5/2014 | Amling et al. | |
| 2002/0120181 A1 * | 8/2002 | Irion | A61B 1/07 |
| | | | 600/178 |
| 2005/0191046 A1 * | 9/2005 | Dehmel | A61B 1/042 |
| | | | 396/17 |
| 2006/0100483 A1 | 5/2006 | Sundet et al. | |
| 2006/0238716 A1 * | 10/2006 | Lee | G02B 27/102 |
| | | | 353/20 |
| 2010/0179384 A1 | 7/2010 | Hoeg et al. | |
| 2010/0217080 A1 * | 8/2010 | Cheung | A61B 1/00135 |
| | | | 600/121 |
| 2013/0158350 A1 * | 6/2013 | Juergens | A61B 1/00112 |
| | | | 600/109 |
| 2014/0051923 A1 * | 2/2014 | Mirza | A61B 1/00126 |
| | | | 600/103 |
| 2015/0305603 A1 * | 10/2015 | Gal | A61B 1/00167 |
| | | | 600/103 |

\* cited by examiner

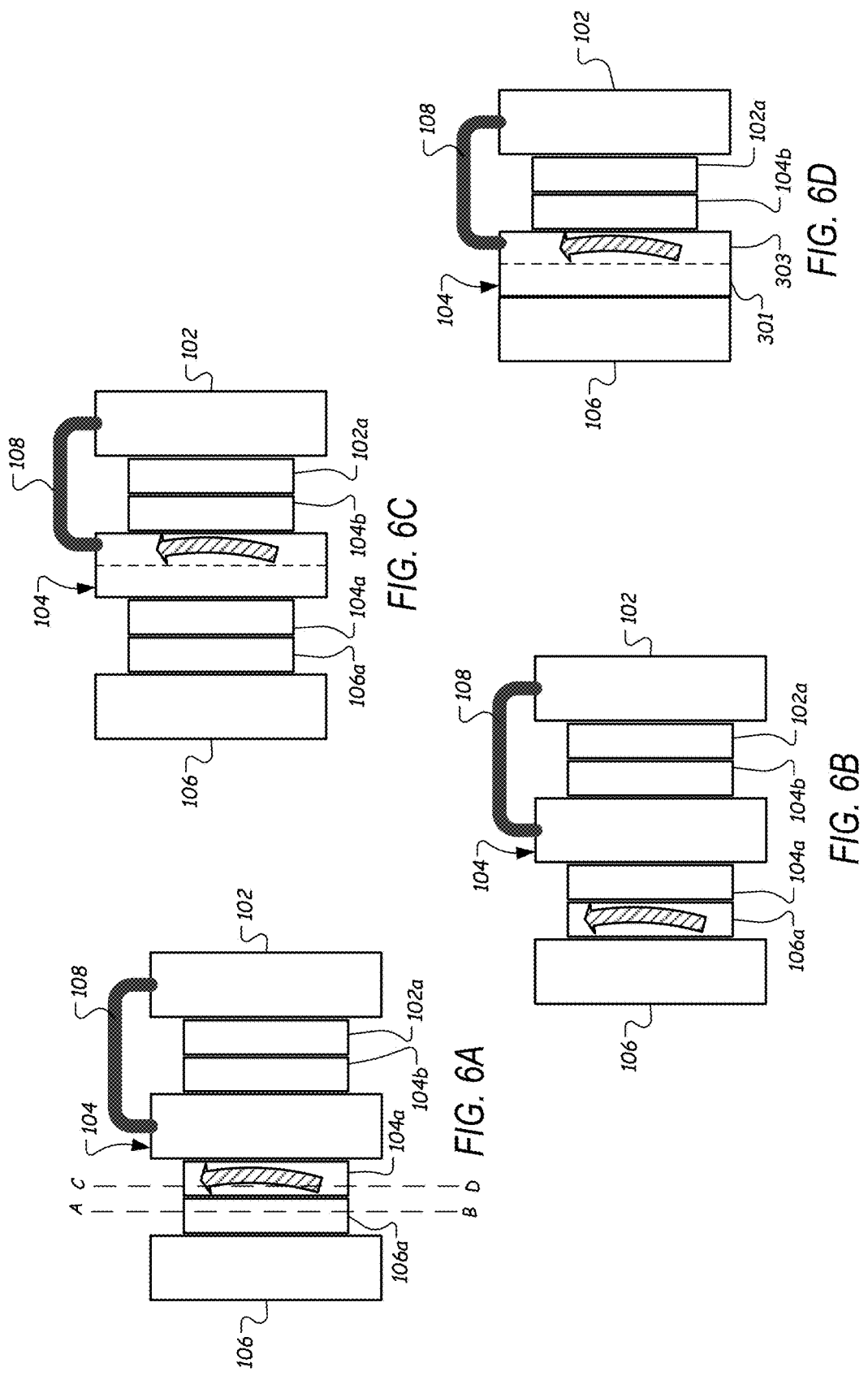

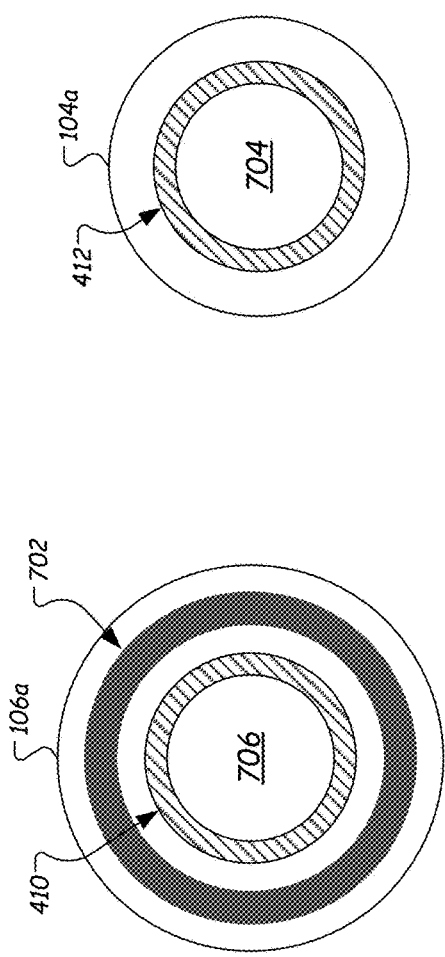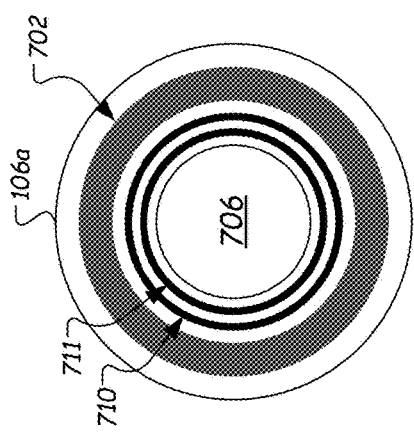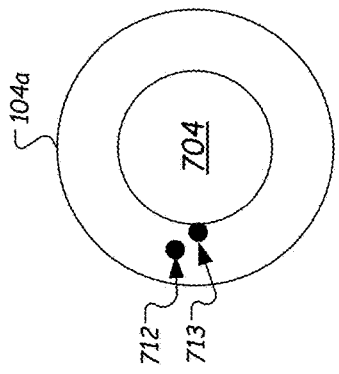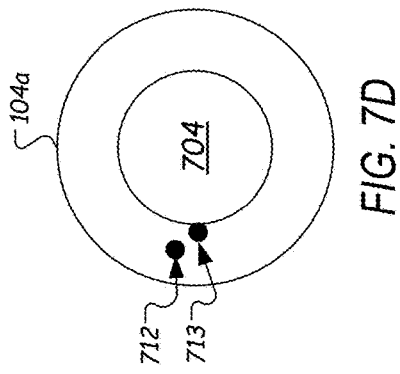

LIGHT DEVICE AND SYSTEM FOR PROVIDING LIGHT TO OPTICAL SCOPES

TECHNICAL FIELD

The present disclosure generally relates to optical scope imaging systems and, more particularly, to light devices for optical scopes having external light ports.

BACKGROUND

Optical scopes such as medical scopes (e.g., endoscopes exoscopes, or other medical examination devices) and industrial scopes (e.g., borescopes), often require an external light source to provide light used to illuminate and examine tissue. An endoscope is an elongated, tubular medical device that is inserted into a body cavity to facilitate visualization and examination by medical professionals. The endoscope may include an optical assembly with an objective lens at its distal end. The optical assembly may include an image-forwarding system, which in rigid scopes is typically a series of spaced-apart lenses. In flexible scopes, the image-forwarding system is typically a bundle of optical fibers.

At the proximal end of the image-forwarding system may be an ocular lens that creates a virtual image for direct human visualization, Often a camera, such as a charge coupled device (CCD) chip or a CMOS device, is mounted to the scope. The camera receives the image and produces a signal for a video display. While doctors can, and often do, look directly into the scope through an ocular lens, it is more common for them to use an attached camera and observe an image on a video screen. The camera (also referred to as a "camera head") is usually detachably connected to the scope. A camera control unit (CCU) is employed to provide, among other controls, a link between the camera head and a video display.

A light source is used to generate light for illuminating an object to be observed by the scope. A light source is often combined in a light source device with its own power source and a control. The light source device may be a separate unit from the scope and connected to the scope's light port.

As the camera head is detachable from the scope, this necessitates a coupling mechanism to transmit, for example, data, power, light, and/or image information between the scope and detachable camera. However, misalignment, dirt/debris, and damage at the coupling location can reduce efficiency of the optical path. In addition, the generation of image information in the scope is difficult because of the corresponding increase in weight when a power source (e.g., a battery) is positioned on the scope and have further drawbacks related to power source lifetime and scope sterilization. Accordingly, it is desirable to have a system that provides for the generation of optical information that does not significantly increase the weight and size of the scope.

Some video scope systems have provided a coupling mechanism between the scope and the camera that includes, for example, a stem/receptacle arrangement for transmitting illuminating light from the camera to the scope and a stem/receptacle arrangement for transmitting image information from the scope to the camera. However, this arrangement does not necessarily provide an easy way to rotate or pan the scope. For instance, as the scope and camera are locked together, the surgeon has to rotate his/her wrist to achieve a panning effect. This only allows for limited rotation since the surgeon's wrist cannot be rotated indefinitely, and causes disorientation of the image as the camera and scope are rotated as a single unit during surgery.

U.S. Publication No. 2014/0210977, now U.S. Pat. No. 8,723,936, the content of which is incorporated reference in its entirety, is owned by the assignee of the present application and discloses, among other things, a light source positioned in an endoscope that is wirelessly powered by a camera. U.S. Pat. No. 8,246,230 discloses a camera that powers a light source adapted to mount on an endoscope light port. U.S. Pat. No. 7,442,167 also discloses a camera that powers a light source adapted to mount on an endoscope light port.

However, the prior art has a number of deficiencies and fails to teach, for example, a camera that powers a light source adapted to mount to a medical scope light port and permits freedom of movement or the scope relative to the camera.

SUMMARY

The needs set forth herein as well as further and other needs and advantages are addressed by the present embodiments, which illustrate solutions and advantages described below.

According to a first aspect of the invention, a system is provided for supplying light to an optical scope having a light port. The system includes a camera having a distal end and an optical axis, referring to an imaginary line along which the camera captures images. A light device has a proximal end attached to the camera, a distal end adapted to be attached to and detached from the optical scope, a light source powered by electrical power received from the camera, and a light cable extending from the light device. The distal end of the light cable is adapted to be attached to and detached from the light port on the optical scope to provide light to the light port. To allow scope rotation, the distal end of the light device is rotatable with respect to the distal end of the camera such that when the light device is attached to the camera, and the optical scope is attached to the light device with the light cable attached to the light port, the light cable and the optical scope are allowed to rotate around the optical axis of the camera.

In some versions, the light device is adapted to be detachable from the camera leaving the camera attachable to another suitable optical scope without the light device. In other versions, the light device is integral to the camera. The optical scope may be, for example, an endoscope, an exoscope, or a borescope.

In some implementations of the first aspect, the camera and light device include transceivers that allow electrical power to be supplied to the light device wirelessly. The electrical power may be transmitted from the camera to the light device by electromagnetic induction. The transceivers may also send and receive control signals. Instead of wireless transceivers, some versions may employ electro-mechanical connections that allow rotation, such as slip rings, to transmit power or control signals. The light source may be adapted to provide light varying in spectral content in response to selected control signals provided through the first and second transceivers.

In further implementations of the first aspect, the light source is further selectively operable to toggle back and forth between two or more illumination modes having different light spectrums, the toggling at a rate greater than a display frame rate, allowing the camera to acquire images alternating images in each mode at a rate greater than a display frame rate. A camera control unit combines the images to display at the display frame rate as illuminated by each spectrum simultaneously. In other implementations of the first aspect, the light source is selectively operable to toggle back and forth between two or more illumination modes having different light spectrums, the toggling at a rate greater than a display frame rate, with the camera operable to acquire images alternating images in each mode at a rate greater than a display frame rate, and the camera control unit operates to process the images to create an image stream which contains data acquired during multiple illumination modes at the display frame rate.

According to a second aspect of the invention, a light device is provided for connecting an optical scope to a camera and supplying light to the optical scope. The light device has a body with an optical portal, the body having a proximal end adapted to be attached to and detached from a distal end of a camera, and a distal end adapted to be attached to and detached from the optical scope, with the optical portal positioned to allow light from the medical scope to pass from the optical scope to a camera light sensor. A light cable is connected to the light device at the light cable's proximal end, and extends from the light device. The light cable's distal end is adapted to be attached to and detached from the light port on the optical scope to provide light to the light port. The distal end of the light device is configured to be rotatable with respect to the distal end of the camera such that when the light device is attached to the camera, and the optical scope is attached to the light device with the light cable attached to the light port, the light cable and the optical scope are allowed to rotate around a central axis of the optical portal. The optical scope for which the light device is adapted to connect the camera and provide light may be selected from a group comprising a medical scope and an industrial scope, for example.

In some implementations according to the various aspects herein, the light source includes a plurality of light emitters with different spectral characteristics, the emitters being selectively activatable to vary the spectral content of the light. The light emitters may be provided as multiple LEDs, including an LED with output peaking at a wavelength shorter than 430 nm, an LED with output peaking between 450 nm and 490 nm, and an LED with substantial output at wavelengths greater than 500 nm. The light source may also be configured to operate in a first mode emitting broadband substantially white light, and further configured to be switched from the first mode to a second mode emitting light of wavelength less than 440 nm and light of wavelength greater than 490 nm but relatively little light between 440 nm and 490 nm.

In further implementations the various aspects herein, the light source may be integrated into the proximal or distal end of the light cable. The light source may include multiple light emitters of having different spectral characteristics, and may also have a beam combiner arranged to receive and combine light from the multiple emitters. The light source may further include an x-cube prism beam combiner having at least three receiving faces, and three light emitters of different spectrums supplying light into the x-cube prism beam combiner. Some variations that are integrated at the end of the light cable may include a light pipe extending from an emitting face of a beam combiner and positioned at the distal end of the light cable such that, when the light cable is attached to the light port of the optical scope, the light pipe optically couples the light source and the light port. A light pipe may optically couple a beam combiner (such as the x-cube prism) and the light port; the optical coupling may be a direct optical coupling (i.e., without intermediary optical components).

According to some implementations of the second aspect, the light device includes a wireless transceiver positioned inside the proximal end of the light device and including a coil adapted to receive electrical power for powering the light device. Instead of wireless transceivers, some versions may employ electro-mechanical connections that allow rotation, such as slip rings, to transmit power or control signals.

In further implementations of the second aspect, the proximal and distal ends of the light device are coupled with a bearing allowing the distal end to rotate relative to the proximal end.

These and other aspects of the invention will be apparent from the following description of example embodiments, considered along with the accompanying drawings.

BRIEF DESCRIPTION OF THE DRAWINGS

FIGS. 6A-D are side view diagrams showing examples of device connections illustrating where rotation may occur in some embodiments.

FIGS. 7A-D are cross-section diagrams showing different versions of electrical connections which allow the light device to rotate.

DETAILED DESCRIPTION OF EXAMPLE EMBODIMENTS

Figure 1:
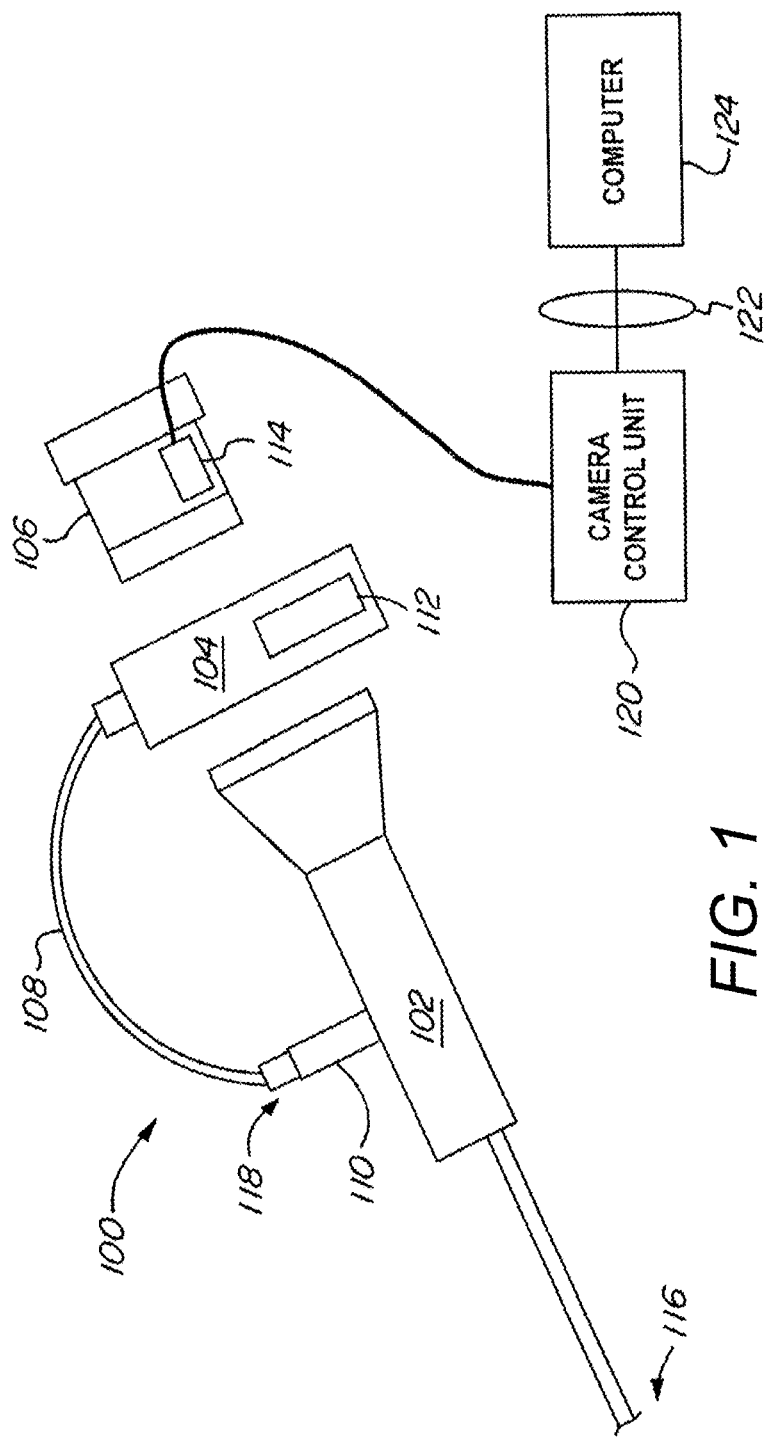
FIG. 1 shows a diagrammatic view of a medical scope light system 100 according to some embodiments herein.

Example embodiments of the present invention are described more fully hereinafter with reference to the accompanying drawings. The following description is presented for illustrative purposes only and the invention should not be limited to these embodiments. For example, wherever "medical scope" is recited, an industrial scope could also be used for purposes of the invention.

The features herein may be employed, for example, to supply illumination for various types of optical scopes such as endoscopes, exoscopes, or other medical examination devices and industrial scopes (e.g., borescopes). In some versions, a camera, scope, and light device are all within the purview of the invention, while other versions provide a light device for use with existing scopes and cameras. In one embodiment, a light device is powered by a camera and has a light cable that can provide illumination to a light port on a conventional endoscope. The light cable may, by electro-mechanical design, rotate freely about the optical axis of the camera head, allowing the endoscope to likewise rotate. The electrical power may be wirelessly received by the light device, although this is not limiting and other versions may include a conductive connection. The electrical power may also be regulated (e.g., by a regulator) so that the electrical power is substantially constant even if integrity of an electrical connection fluctuates.

Many prior art scope systems without an integrated light source rely on the use of external light sources that employ fiber optic cables, LEDs with battery packs, and LEDs on non-integrated cables connected to external power supplies (such as a CCU).

According to the present teachings, a light cable may incorporate a light source (e.g., one or more LEDs) and couple to the light port of a conventional endoscope. The light source may be at the distal end of the light cable. The light cable may be rotatably coupled to a camera head (e.g., rotate freely about the optical axis of the camera head and medical scope) and wirelessly receive power from the camera. The light source employed with various embodiments herein may be an LED, multiple LEDs, including LEDs with phosphors, any one or more of a variety of visible or invisible light or radiation sources, including, but not limited to, laser sources such as lasers, laser diodes or other semiconductor lasers, incandescent sources (e.g., filament lamps, halogen lamps), fluorescent sources, phosphorescent sources, high intensity discharge sources (e.g., sodium vapor, mercury vapor, and metal halide lamps), and other types of luminescent sources.

While in one embodiment the light source may be powered wirelessly (e.g., inductively), in other embodiments other mechanical structures may be used. For example, a slip ring may be used. A slip ring is an electromechanical device that allows the transmission of power and electrical signals from a stationary to a rotating structure. This is typically realized when a stationary contact rubs against a rotating conductive ring as it moves, maintaining a conductive connection. The connection can provide electrical power as well as analog or digital signals.

FIG. 1 shows a diagrammatic view of a medical scope light system 100 according to some embodiments herein. A light device 104 may be detachably connected to both a medical scope 102 and a camera 106. The depicted camera 106 ("camera head", "camera") includes a housing which may have operating controls, and a light sensor array ("sensor") presented toward its distal face to detect visible images or fluoresced imaging ("FI") images from a medical scope (not shown in FIG. 1). A transceiver 114 (or other power port) on the camera 106 may send electrical power to a transceiver 112 (or other power port) on the light device 104. The transmission of power may be performed wirelessly or wired if a mechanical connection is used (e.g., a slip ring). The transceivers 112 and 114 may also be adapted to transmit and receive control signals between camera 106 and light device 104, to activate and deactivate the light, control the intensity, and in some cases control multiple light emitters or control the spectrum of the light as further described below. In some embodiments, transceivers 112 and 114 are wireless power devices that operate through a pair of inductive coils compatible with a wireless power standard such as Qi (pronounced "chee") protocol from the Wireless Power Consortium, or one of the Airfuel Alliance wireless power protocols. Protocols such as these allow extensions to the power control signaling allowing data signaling to be transmitted over the link for a particular application. Construction of such power transfer circuits and signaling circuits is known in the art and will not be further described here. In some embodiments, a short range wireless communication protocol may be used separately from the wireless power source. In such cases, near-field protocols are desired to avoid interference and erroneous signaling with other medical devices near the operating area. One such protocol is the IEEE 1902.1 "RuBee" protocol.

The light device 104 may have a light cable 108 that may be attached to and detached from a light port 110 of the medical scope 102 at distal end 118 of the light device 104.

While a light post-style light port 110 is shown because it is the most common arrangement, some medical scopes employed with various embodiments may not have a light post, but instead use a recessed port or some other form of light port. The light port is preferably presented on the medical scope along its body between the scope's proximal and distal ends, and therefore rotates around with the exterior of the scope body when the scope is rotated. The rotating electrical connection or wireless electrical connection between camera 106 and light device 104, allows the light cable to rotate freely about the optical axis of the camera head, allowing the endoscope to likewise rotate.

In operation, the light device 104 is connected to and powered by the camera 106, for example, wirelessly by using transceivers 112,114, Light generated by a light source of the light device 104 is transmitted through the light port 110 of the medical scope 102 and through optical channels such as fiber-optics to scope 102's distal end 116 where it is emitted to reflect off a subject scene at which the medical scope is pointed. Images or incident light captured from the distal end 116 of the medical scope 102 may then be transmitted optically through a hole or other optical portal formed through the body of light device 104 where the image light is then incident on the sensor of camera 106, where the sensor produces electrical signals which are processed and ultimately fed to a camera control unit 120. The body of light device 104 may include optical elements such as one or ore lens, achromats, apochromats, or rod lenses to ensure a proper focal distance is maintained relative to the medical scope 102 eyepiece or viewing end. The camera control unit 120 may also be in communication with a computer 124 over a network 122.

Figure 2:
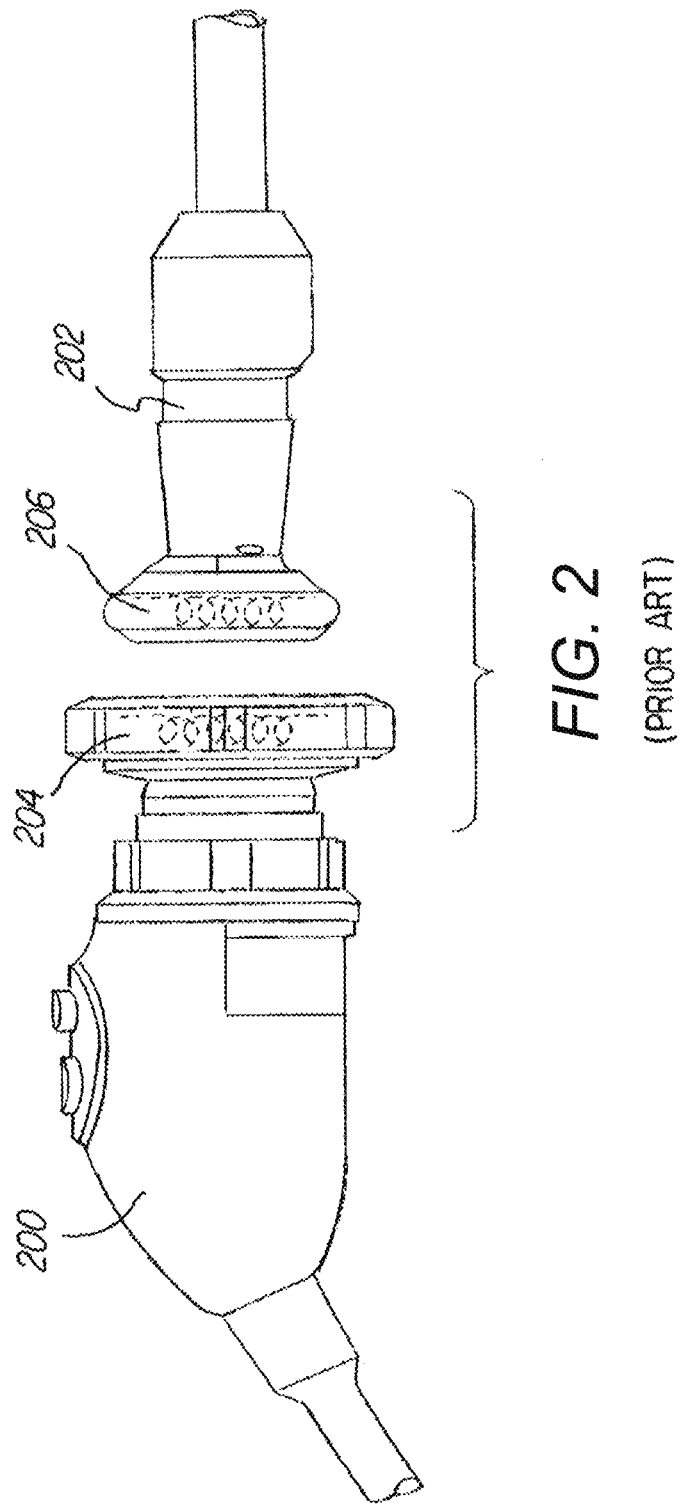
FIG. 2 is a side view of a prior art system where a camera wirelessly powers a light source in an endoscope.

Referring now to FIG. 2, shown is a side view of a prior art system where a camera 200 wirelessly powers a light source in an endoscope 202, providing a rotatable wireless power coupling to endoscope 202. As shown, there is an inductive coil 204 in the camera head 200 and an inductive coil 206 in the endoscope 202. By use of the inductive coils 204, 206 a light source in the endoscope 202 may be wirelessly powered.

This prior art camera system is limited because it still requires an external light source if the user wishes to use a conventional endoscope. Conventional endoscopes do not have integrated light sources but instead have light posts for receiving light cables, According to the present teachings, camera heads with induction coils may be used to supply light to conventional endoscopes having light ports (e.g., endoscopes without induction capabilities).

Figure 3:
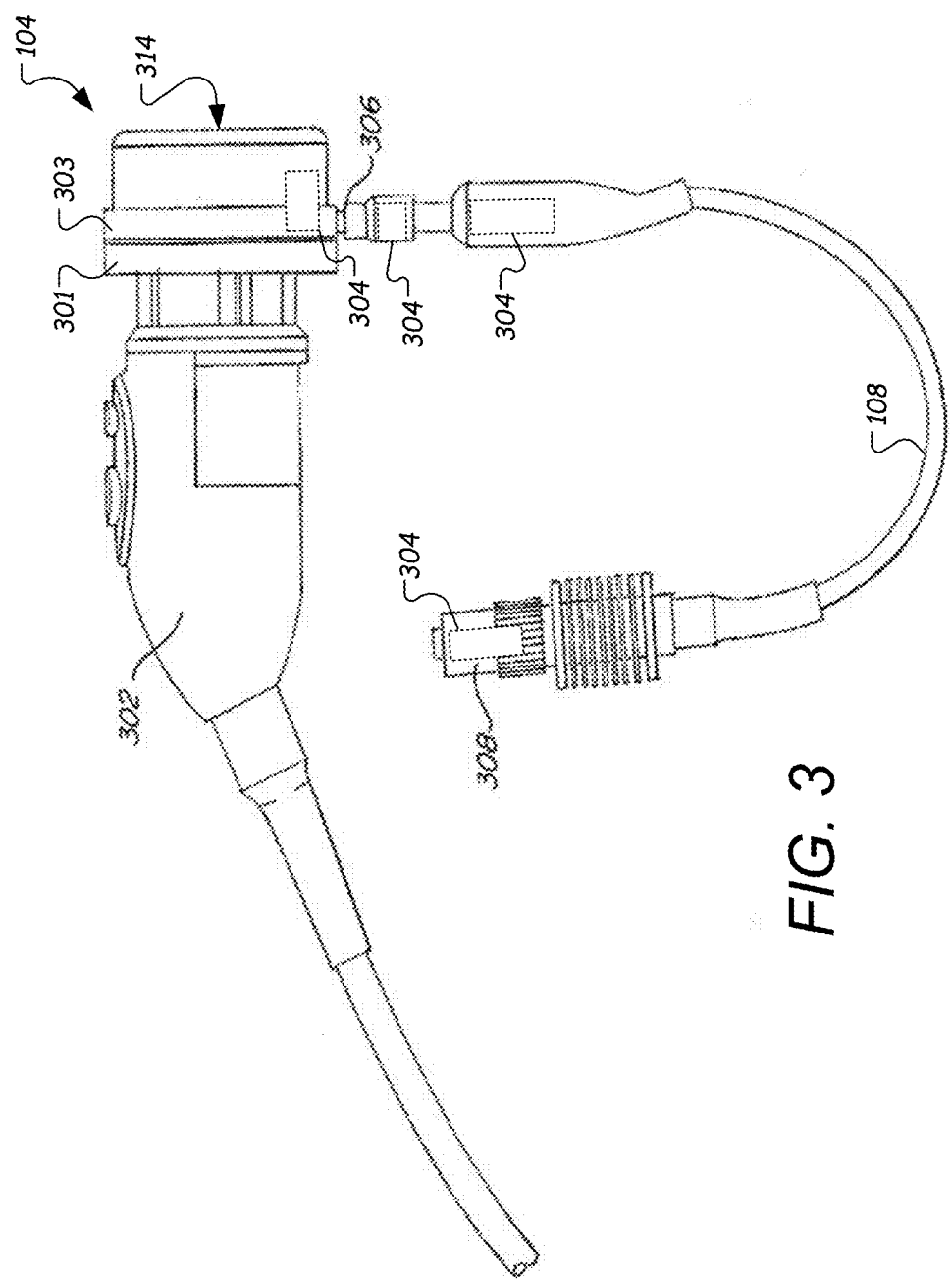
FIG. 3 is a side view of another embodiment of a light device attached to a camera.

Referring now to FIG. 3, shown is a side view of one embodiment of the light device 104 according to FIG. 1 attached to a camera head 302. In this version, light device 104 includes rotating components which are integral to the camera head 302, meaning they are not detachable and re-attachable in the normal course of operation, but instead are assembled with the body of camera 302. In this embodiment, light device 104 has a proximal end 301 attached to the distal end of camera 302. Light device 104 also includes a distal end 303 which is rotatably connected to proximal end 301, preferably with one or more bearings, making distal end 303 rotatable with respect to the distal end of camera 302. Distal end 303 also includes a scope coupling presented along its distal face 314 into which a medical scope may be attached. The coupling is typically formed to receive an eye cup like those commonly used on medical scopes such as endoscopes and borescopes. However, the type of coupling is not limited other scopes designed to be used with cameras may have other attachment structures designed to couple the scope to a camera. As such, light device 104 may include a suitably-designed scope coupling for various types of scopes.

Light device 104, in this version, further includes an optical portal or hole formed centrally and aligned with the optical axis of the camera 302 sensor, and constructed such that light passing from a connected medical scope will pass through the optical portal or hole and to the camera 302 sensor. The portal or hole may include an air gap for transmitting light from the endoscope to the camera, or may include optical elements such as achromats, apochromats, rod lenses and other lenses. Further, the portal may include or more planar or curved cover slips, through which light passes through the light device.

Figure 4:
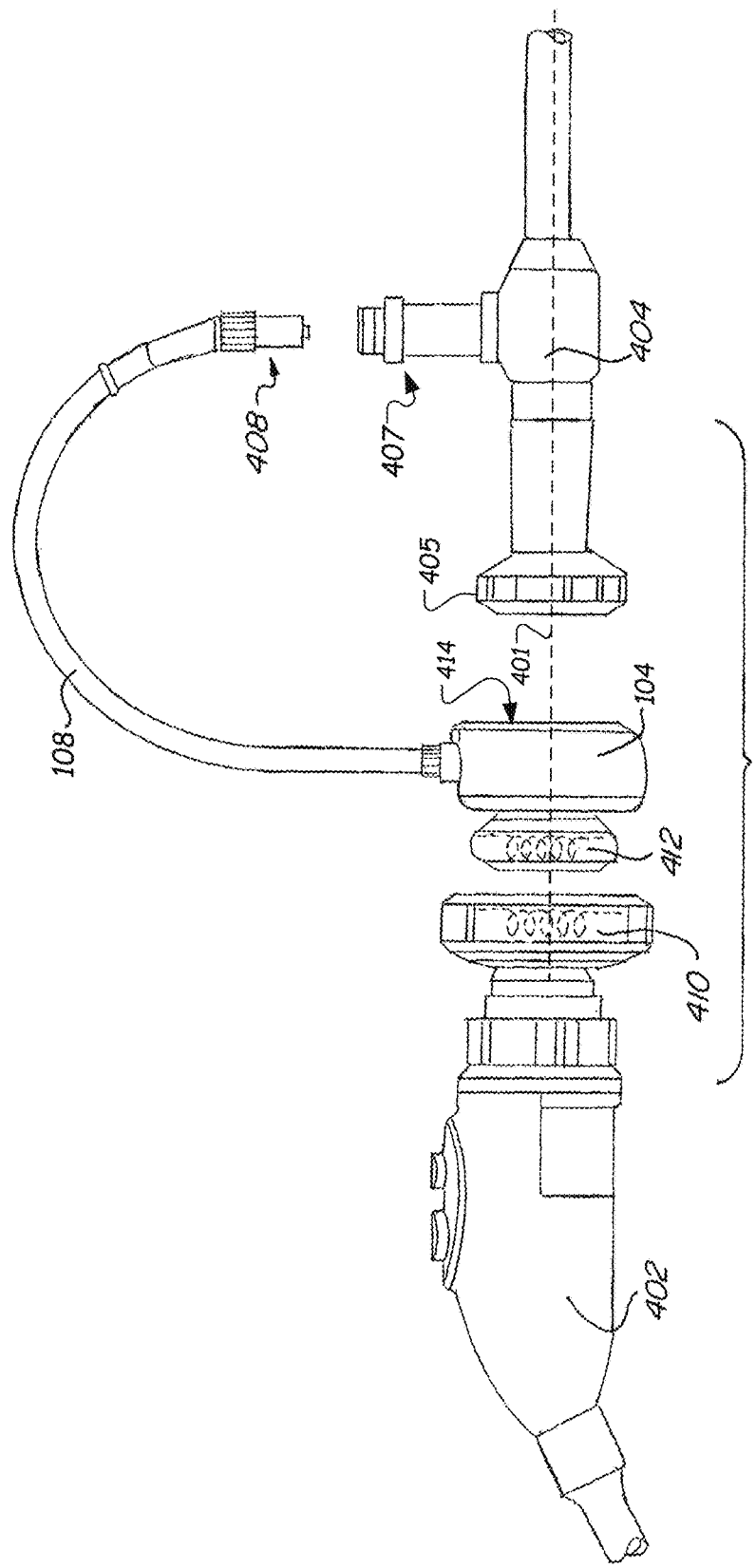
FIG. 4 is a side view of another embodiment of a light device depicted as detached from a camera and an endoscope.

By presenting a scope coupling on the light device 104's rotatable distal end 303, light device 104 allows that when a medical scope is attached to light device 104 with the light cable 108 attached to the medical scope light port, the light cable and the medical scope are allowed to rotate around the optical axis of the camera. Accordingly, in some versions the light cable 108 may be integral with light device 104 and may not be detachable, while in other versions a light cable connector 306 may be provided on light device 104's rotating distal end 303 allowing light cable 108 to be disconnectable and interchangeable with another type of light cable. As described herein, the electromechanical design allows free rotation around the optical axis of camera head 302 of a light cable to the light device 104 while maintaining the electrical coupling to the light device to power and control the light source. A light source 304 is shown in several alternative positions by a dotted box, and may be positioned inside the distal end of light cable 108, inside the proximal end of light cable 108, or inside the distal end 303 of light device 104 or coupled between the distal end 303 and light cable 108. If light source 304 is not integrated with the distal end of light cable 108, the light cable includes suitable fiber-optic connection and couplings are included to conduct light from the light source to the distal end coupling 308. The light cable may have a coupling 308 that allows the distal tip to couple to a conventional scope light port or light post (such as shown in FIGS. 1 and 4). In this way, a camera 302 may be used to supply power to a light source 304 and in turn provide light to a conventional optical scope like an endoscope having a light post, while allowing the scope to be rotated about the camera's optical axis as needed for the operator to adjust the view and position of the scope, without being limited by the light cable curling around the camera or scope.

Referring now to FIG. 4, shown is a side view of another embodiment of light device 104 according to FIG. 1 depicted as detached from a camera 402 and an endoscope 404. In this embodiment, camera 402 includes at its distal end an electro-mechanical coupling 410 designed to receive a proximal end coupling 412 of light device 104, or to receive the eye cup or proximal end 405 of an endoscope such as scope 404. In this manner, camera 402 may be made compatible both with endoscopes that have an integrated light source which can be powered through an inductive coupling such as that shown in FIG. 2, and endoscopes without an integrated light source, which require light coupled in through an external light port like the depicted light post 407. Light device 104 may have a light source integrated at the distal end 408 of light cable 108. However, the light source could also be integrated into the camera body 402 and a light guide (e.g., fiber optics) used to convey light through the light device 104. The light device electronics and light emitters may also be integrated into light device 104 at other locations as depicted with regard to FIG. 3. By use of couplings 410 and 412, or another suitable electromechanical connection, light device 108 is detachable and reattachable to the camera in the normal course of use. The attachment mechanism may be a snap in mechanical coupling, a clasp or grasping mechanism on the camera side such as that typically used to grasp a scope. The attachment mechanism may also be a screw in connection or a rigid connection with screws, providing it is detachable and reattachable in a clinical setting and camera 402 is usable with or without light device 104, depending of course on the compatibility of the scope such as endoscope 404.

Light device 104 is also adapted to attach and detach from endoscope 404 using a grasping mechanism or other coupling, preferably formed as a receptacle presented toward the distal face 414 of light device 104. Endoscope 404 can be held at the coupling by means of holding claws, for example in a clamping, force-fit or frictionally engaged or interlocking manner. Because the light device itself provides the rotatable connection to camera 402, a further rotatable connection between light device 104 and endoscope 404 is not necessary. The connection between light device 104 and endoscope 404 is preferably one without slip, allowing for suitable transmission of torque. The coupling at face 414 can therefore be constructed with a locking mechanism or other suitable grasping device that can rigidly hold endoscope 404 with its optical axis in alignment with the central portal of light device 104, so that when light device 104 is connected to camera head 402, the camera optical axis 401 is aligned with the light device portal and the optical axis of endoscope 404. The camera 402, light device 104, and endoscope 404 are shown detached, but in use are attached with the light device 104 proximal end coupled to the camera 402 distal end, placing coils at couplings 410 and 412 adjacent to each other for power and control signals to be coupled. Endoscope 404 in the connected state is inserted into the light device 104 coupler at face 414, which may be locked or otherwise fixed to rigidly hold endoscope 404. Also in the connected state, the distal end 408 of light cable 108 is connected to light post 407. In the connected state, light device 401 allows rotation of the light device and scope around the optical axis 401. The body of the couplings at 410, 412, 414 and 405 may be constructed of metal, a rigid polymer, composites thereof, or other suitable rigid material. If coils are integrated as shown in FIG. 4, the coil is typically embedded in an epoxy or other dielectric or insulator.

The light device 104 may have an inductive coil such as that shown at coupling 412 that couples to an inductive coil such as that shown at coupling 410 on the camera head 402 and receives power from the camera head 402 through the transceivers 112 and 114 (FIG. 1). In this way, the camera head 402 may be used to wirelessly power light provided to a conventional endoscope 404. This not only allows the use of camera heads having inductive coils with conventional endoscopes, and thus not requiring an external light source, but also allows the endoscope to freely rotate about the optical axis of the camera (e.g., axis 401 extending perpendicularly from the camera lens or sensor at its distal end).

Figure 5:
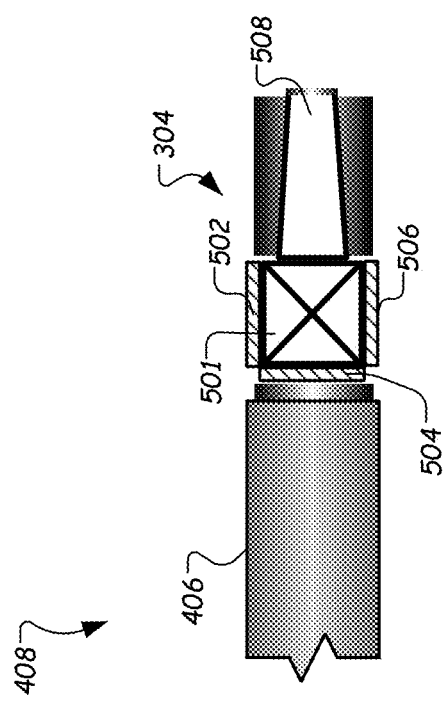
FIG. 5 is a cutaway cross-sectional view of a cable distal end according to another example embodiment.

FIG. 5 shows a cross-sectional cutaway view of an example light source 304 integrated into the distal end 408 of a light cable. In this embodiment, an adjustable spectrum light source 304 is provided, the light source adapted to provide light in varying in spectral content in different modes. The different modes may be selected and controlled through the first and second transceivers as described with respect to FIG. 1. Wires or flexible circuits connect light source 304 to the control and power circuitry in the body of light device 104. In the depicted embodiment, the light source 304 includes a plurality of light emitters 502, 504, and 506 with different spectral characteristics, the emitters being selectively activated to vary the spectral content of the light. In a preferred version the light emitters are multiple LEDs, including at least two light emitters of having different spectral characteristics, from which emitted light is directed into a beam combiner such as the depicted x-cube prism beam combiner 501 to mix or combine the light from each emitter. Other suitable beam combiners may be used. The output of beam combiner 501 is directed to a light pipe 508, which presents a face toward the distal tip of the light cable for direct coupling to a light port. Other versions may not use a light pipe. For example, when light source 304 is integrated in the proximal end of light cable 108, or in the body of light device 104, fiber optics are used to carry the emitted light to the distal end of light cable 108.

The light emitters in this version include a violet LED 504 with output peaking at a wavelength shorter than 430 nm, a blue LED 506 with output peaking between 450 nm and 490 nm, and a lime or amber LED 502 with substantial output at wavelengths greater than 500 nm. While LEDs are shown, laser diodes or other suitable devices may be employed. While a violet LED is used in this version, other versions may use the more common red LED or emitter. The violet is selected here to provide ability for light source 304 to operate in a first mode emitting broadband substantially white light by activating all of the emitters, and further to be switched from the first mode to a second mode emitting light of wavelength less than 440 nm and light of wavelength greater than 490 nm but relatively little light between 440 nm and 490 nm (no light or light at much less power, for example, at least 3 db, 6 db, 9 db, or 12 db below the power level of the other bands), by turning off the blue emitter and activating the other two emitters. Light with such a "band gap" has been found to bring out or emphasize details not easily discernable under white light. LEDs with phosphors may be used to achieve the desired spectral components for the violet LED, and may be used for the other emitters as well. In some versions, a second mode is provided that excludes other selected portions of the visible wavelength bands. Further, in some versions a mode is provided that provides a narrow band light, for example by activating only one emitter or LED. In some versions, light source 304 may include one or more emitters for non-visible light, such as infra-red or ultra-violet.

Light source 304 may also be used to toggle back and forth between different modes at a high rate of speed, for example to change modes at the camera frame rate which may be 20 fps, 30 fps, 60 fps, or other desirable frame rates to which the camera may be set, allowing every other frame to be captured with a different light mode. This may be used to create two video streams showing the different light modes. Light source 304 may also toggle faster than the camera frame rate, with the camera being controlled to acquire images alternating images in each mode at a rate greater than a display frame rate. A camera control unit such as unit 120 (FIG. 1) may then combine the images to display at the display frame rate as illuminated by each spectrum simultaneously. Or, the camera control unit may be operated to process the images to create an image stream which contains data acquired during multiple illumination modes at the display frame rate.

FIGS. 6A-6D are block diagram views of several example embodiments showing where a rotating connection may be implemented. In FIG. 6A, camera 106 is shown connected to light device 104 through a coupling on the camera side (106*a*) which receives a coupling from the light device side (104*a*). Light device 104 is shown coupled to medical scope 102 through a coupling on the light device side (104*b*) which receives a coupling from the medical scope side (102*a*). Light cable 108 is also shown connected from light device 104 to medical scope 102. The depicted arrow on light device coupling 104*a* shows where the rotating connection is made in this version. That is, the coupling 104*a* rotates with respect to the connected camera coupling 106*a*, allowing everything to the right of coupling 104*a* to rotate with respect to the optical axis of camera 106.

FIG. 6B shows a similar arrangement to that of FIG. 6A, except that the rotation occurs at the camera coupling 106*a*. That is, the coupling 106*a* rotates with respect to the camera, allowing everything to the right of 106*a* to also rotate around the camera 106 optical axis. Such an arrangement may be useful, for example, where a light device 104 and scope 106 have a combined mass that may make a rotating detachable coupling at 104*a* unstable. Further, such an arrangement allows for a rigid, no slip, grasping mechanism between couplings 106*a* and 104*a*.

FIG. 6C shows another alternative arrangement in which the rotation mechanism is provided in the body of light device 104, as shown by the dotted line splitting light device 104. Light cable 108 is attached on the rotating portion of light device 104 allowing it to rotate with scope 102.

FIG. 6D shows another alternative arrangement in which the light device 104 is integrated with camera 106, such as the arrangement of FIG. 3, As can be seen, light device 104 has a distal portion 303 that rotates with respect to a proximal portion 301, allowing distal portion 303 and all components to the right of it to rotate with respect to the optical axis of camera 106.

FIGS. 7A and 7B are two cross-sectional diagrams showing the connectors on the camera (106*a*) and the light device (104*a*) of FIG. 6A including an inductive coil for coupling power. FIG. 7A shows the cross section along dotted line A-B of FIG. 6A, and FIG. 7A shows the cross section along line C-D. The camera 106 in this version has a coupling 106*a* which includes a mechanical connector or receptacle 702 such as a scope grasping mechanism, clamp, or other suitable connector. Coupling 106*a* also includes an inductive coil 410, typically embedded in a resin, which is electrically connected to transceiver electronics to couple power and/or control signals to the corresponding coil 412 on the light device 104's coupling 104*a*.

FIGS. 7C and 7D are alternative cross-section diagrams along the same lines A-B and C-D, showing an embodiment of couplers 106*a* and 104*a* that employ mechanical slip ring connections. In FIG. 7C, the camera side coupler 106*a* is shown with a mechanical connector 702 and two slip ring electrical connections 710 and 711. These connections are typically conductive rings such as copper presented along the outer face of the coupler 106*a*. As the light device coupler 104*a* of FIG. 7D is attached to coupler 106*a*, the two electrical contacts 712 and 713 touch slip rings 710 and 711 respectively, and slide along the surface of the slip rings while maintaining electrical contact to allow both power and control signals to be transmitted by the respective transceivers. Contacts 712 and 713 may be brushes, springs, spring loaded contacts, or other suitable slip ring contacts. The transmission protocol employed may be selected from any suitable 2-wire power and communication protocol. Construction of slip rings and their protocols are known in the art and will not be further described here.

The examples of FIGS. 7A-7D are shown with respect to a rotating connection provided at the coupling of light device 104 and camera 106, however similar connections may be employed at a rotating connection made at other locations as depicted in FIGS. 6B, 6C, and 6D, for example.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A system for providing light to an optical scope having a light port, the system comprising:
   a camera having a distal end and an optical axis extending from its distal end;
   a light device including:
      a proximal end attached to the camera;
      a distal end adapted to be attached to and detached from the optical scope;
      a light source powered by electrical power received from the camera; and
      a light cable extending from the light device and having a distal end adapted to be attached to and detached from the light port on the optical scope to provide light to the light port;
   wherein the distal end of the light device is rotatable with respect to the distal end of the camera such that when the light device is attached to the camera, and the optical scope is attached to the light device with the light cable attached to the light port, the light cable and the optical scope are allowed to rotate around the optical axis of the camera; and
   wherein the camera comprises a first transceiver; and the light device comprises a second transceiver that wirelessly couples to the first transceiver when brought in proximity thereto and wirelessly receives the electrical power from the first transceiver; the first transceiver further adapted to transmit control signals to the light device, and the second transceiver further adapted to receive the control signals;
   wherein the light source comprises a plurality of light emitters with different spectral characteristics, the emitters being selectively activatable to vary the spectral content of the light in response to selected control signals provided through the first and second transceivers, the light source being integrated into the distal end of the light cable, and further includes a light pipe extending from an emitting face of a beam combiner and positioned at the distal end of the light cable such that when the light cable is attached to the light port of the optical scope, the light pipe optically couples the light source and the light port.

2. The system of claim 1, wherein the electrical power is transmitted from the camera to the light device by electromagnetic induction.

3. The system of claim 1, in which the plurality of light emitters further comprises multiple LEDs, including an LED with output peaking at a wavelength shorter than 430 nm, an LED with output peaking between 450 nm and 490 nm, and an LED with substantial output at wavelengths greater than 500 nm.

4. The system of claim 1, in which the light source is configured to be operated in a first mode emitting broadband substantially white light, and further configured to be switched from the first mode to a second mode emitting light of wavelength less than 440 nm and light of wavelength greater than 490 nm but relatively little light between 440 nm and 490 nm.

5. The system of claim 4 in which the light source further comprises an x-cube prism beam combiner having at least three receiving faces and further wherein three light emitters of different spectral characteristics are arranged at respective receiving faces of the beam combiner.

6. A system for providing light to an optical scope having a light port, the system comprising:
   a camera having a distal end and an optical axis extending from its distal end;
   a light device including:
      a proximal end attached to the camera;
      a distal end adapted to be attached to and detached from the optical scope;
      a light source powered by electrical power received from the camera; and
      a light cable extending from the light device and having a distal end adapted to be attached to and detached from the light port on the optical scope to provide light to the light port;
   wherein the distal end of the light device is rotatable with respect to the distal end of the camera such that when the light device is attached to the camera, and the optical scope is attached to the light device with the light cable attached to the light port, the light cable and the optical scope are allowed to rotate around the optical axis of the camera;

wherein the camera comprises a first transceiver; and the light device comprises a second transceiver that wirelessly couples to the first transceiver when brought in proximity thereto and wirelessly receives the electrical power from the first transceiver by electromagnetic induction; the first transceiver further adapted to transmit control signals to the light device, and the second transceiver further adapted to receive the control signals;

wherein the light source comprises a plurality of light emitters with different spectral characteristics, the emitters being selectively activatable to vary the spectral content of the light in response to selected control signals provided through the first and second transceivers, and wherein the light source is further selectively operable to toggle back and forth between two or more illumination modes having different light spectrums, the toggling at a rate greater than a display frame rate, with the camera operable to acquire alternating images in each mode at a rate greater than a display frame rate, and a camera control unit operable to process the images to create an image stream which contains data acquired during multiple illumination modes at the display frame rate.

7. The system of claim 6, wherein the camera control unit is operable to combine the images to display at the display frame rate as illuminated by each spectrum simultaneously.

8. The system of claim 6, wherein the light source is arranged integrated into the proximal or distal end of the light cable and includes a beam combiner arranged to receive and combine light from the plurality of light emitters.

9. The system of claim 6, wherein the light device is adapted to be detachable from the camera leaving the camera attachable to another suitable optical scope without the light device.

10. The system of claim 6, wherein the light device is integral to the camera.

11. A system for providing light to an optical scope having a light port, the system comprising:
    a camera having a distal end and an optical axis extending from its distal end;
    a light device including:
        a proximal end attached the camera;
        a distal end adapted to be attached to and detached from the optical scope;
        a light source powered by electrical power received from the camera; and
        a light cable extending from the light device and having a distal end adapted to be attached to and detached from the light port on the optical scope to provide light to the light port;
        wherein the light source is further selectively operable to toggle back and forth between two or more illumination modes having different light spectrums, the toggling at a rate greater than a display frame rate, with the camera operable to acquire alternating images in each mode at a rate greater than a display frame rate; and
    a camera control unit operable to process the images to create an image stream which contains data acquired during multiple illumination modes at the display frame rate.

12. The system of claim 11, wherein the camera control unit is operable to combine the images to display at the display frame rate as illuminated by each spectrum simultaneously.

13. The system of claim 11, in which the light source is configured to be operated in a first mode emitting broadband substantially white light, and further configured to be switched from the first mode to a second mode emitting light of wavelength less than 440 nm and light of wavelength greater than 490 nm but relatively little light between 440 nm and 490 nm.

14. The system of claim 11, wherein the light device is adapted to be detachable from the camera leaving the camera attachable to another suitable optical scope without the light device.

* * * * *